(12) United States Patent
Winters et al.

(10) Patent No.: US 6,569,186 B1
(45) Date of Patent: May 27, 2003

(54) SOFT TISSUE SCREW AND FIXATION DEVICE

(75) Inventors: Thomas F. Winters, Winterpark, FL (US); James A. Boucher, Warsaw, IN (US); Cory R. Schaffhausen, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 194 days.

(21) Appl. No.: 09/680,807

(22) Filed: Oct. 5, 2000

(51) Int. Cl.$^7$ ................................................ A61B 17/04
(52) U.S. Cl. ........................ 606/232; 606/73; 606/104
(58) Field of Search ...................... 606/60, 65–66, 606/73, 232–233, 72

(56) References Cited

U.S. PATENT DOCUMENTS

| | | | |
|---|---|---|---|
| 4,988,351 A | | 1/1991 | Paulos et al. |
| 5,269,784 A | * | 12/1993 | Mast ........................... 606/69 |
| D374,287 S | * | 10/1996 | Goble et al. ................ D24/145 |
| 5,569,252 A | | 10/1996 | Justin et al. |
| D375,791 S | * | 11/1996 | Goble et al. ................ D24/145 |
| 5,601,558 A | * | 2/1997 | Torrie et al. ................. 411/495 |
| 5,718,706 A | * | 2/1998 | Roger ......................... 606/104 |
| 5,720,753 A | * | 2/1998 | Sander et al. ............... 606/104 |
| 5,730,744 A | | 3/1998 | Justin et al. |
| 5,733,307 A | * | 3/1998 | Dinsdale ...................... 606/104 |
| D404,128 S | * | 1/1999 | Huebner ..................... D24/145 |
| 5,961,521 A | * | 10/1999 | Roger ......................... 606/151 |
| 6,027,523 A | * | 2/2000 | Schmieding ................ 606/232 |
| 6,056,752 A | * | 5/2000 | Roger ......................... 606/151 |
| 6,096,060 A | * | 8/2000 | Fitts et al. .................... 606/232 |
| 6,123,711 A | | 9/2000 | Winters |
| 6,231,606 B1 | * | 5/2001 | Graf et al. .................... 606/72 |
| 2001/0007074 A1 | * | 7/2001 | Strobel et al. ............... 606/73 |

* cited by examiner

Primary Examiner—David O. Reip
Assistant Examiner—D Jacob Davis
(74) Attorney, Agent, or Firm—Harness, Dickey & Pierce, P.L.C.

(57) ABSTRACT

A fixation device for engaging the soft tissue in a body. The fixation device includes a body portion and a plurality of teeth. The body portion has a proximal face, a distal face, a central aperture and a suture slot. The central aperture is formed through the proximal and distal faces and is configured to receive a screw. The suture slot intersects the central aperture and is configured to receive a suture. The plurality of teeth coupled to the proximal face of the body portion and are configured to engage the soft tissue. A soft tissue securing device and a method for securing soft tissue to a bone are also provided.

20 Claims, 6 Drawing Sheets

SOFT TISSUE SCREW AND FIXATION DEVICE

TECHNICAL FIELD

The present invention relates generally to medical devices and methods for securing body tissues and more particularly to a method and device for securing soft tissue to bone.

BACKGROUND OF THE INVENTION

Background Art

It is commonplace in arthroscopic procedures to employ suture anchors and tacks to secure soft tissues to bone. Despite their widespread use, several drawbacks have been noted with these techniques. Suture anchors, for example, are often undesirable as they require the surgeon to tie a plurality of knots to secure the soft tissue to the bone. The procedure of tying knots can be very time consuming, thereby increasing the cost of the procedure and limiting the capacity of the surgeon. Furthermore, the strength of the repair is limited by the strength of the knot. This latter drawback is of particular significance if the knot is tied improperly as the strength of the knot in such situations can be significantly lower than the tensile strength of the suture material.

Barbed or expanding tacks are often times not desirable due to the difficulty of their removal should the surgeon decide that they have not been positioned correctly after their insertion into the bone. Furthermore, it is generally not possible to "fine-tune" the degree of compression that the tack exerts onto the soft tissue. If the tack is implanted too deeply and compresses the soft tissue to a higher degree than that which is desired, it is not possible to back the tack out of the hole in the bone to relieve the pressure exerted onto the soft tissue.

Many of the known tacks are formed with a round head or are used in conjunction with a washer. In some situations, such as the attachment of soft tissue to the glenoid rim, tacks having these configurations can protrude past the bone and impinge upon other bones in the joint (e.g., the humeral head) when the bones in the joint are moved relative to one another.

SUMMARY OF THE INVENTION

In one preferred form, the present invention provides a fixation device for engaging the soft tissue in a body. The fixation device includes a body portion and a plurality of teeth. The body portion has a proximal face, a distal face, a central aperture and a suture slot. The central aperture is formed through the proximal and distal faces and is configured to receive a screw. The suture slot intersects the central aperture and is configured to receive a suture. The plurality of teeth coupled to the proximal face of the body portion and are configured to engage the soft tissue.

In another preferred form, the present invention provides a tissue securing device for securing soft tissue to a bone. The soft tissue securing device includes a suture, a fixation device and a screw. The suture has a looped section and a pair of ends. The fixation device has a body portion, a plurality of teeth and a suture guide. The body portion includes a proximal face, a distal face, a central aperture and a suture slot. The central aperture is formed through the proximal and distal faces and configured to receive the screw. The suture slot intersects the central aperture and receives the looped section of the suture. The plurality of teeth are coupled to the proximal face of the body portion and are configured to engage the soft tissue. The suture guide is coupled to the proximal face of the body portion and extends between the ends of the suture slot. The screw is disposed through the central aperture and abuts the suture guide. The suture guide guides the suture around a side of the screw in response to the application of tension to the ends of the suture.

In another preferred form, the present invention provides a method for securing soft tissue to a bone. The method includes the steps of: providing a drill having a guide aperture formed therethrough along a longitudinal axis of the drill; providing a guide member having a driver portion, the driver portion having a non-circular cross section; inserting the guide member into the guide aperture; forming a hole in the bone with the drill; translating the guide member into the hole; removing the drill from the hole while maintaining the guide member in the hole; providing a soft tissue securing device having a fixation device and a screw, the fixation device having a body portion with a proximal face and a central aperture, the screw having a threaded portion and a hollow cavity configured to mate with the driver portion, the hollow cavity being formed through the screw and having a portion with a non-circular cross section, the screw being disposed through the central aperture; aligning the hollow cavity to the guide member; translating the screw along the guide member and into contact with the bone; and rotating the guide member so that driver portion rotates the screw thereby causing the threaded portion of the screw to threadably engage the bone and exert a clamping force onto the fixation device to secure the soft tissue to the bone.

BRIEF DESCRIPTION OF THE DRAWINGS

Additional advantages and features of the present invention will become apparent from the subsequent description and the appended claims, taken in conjunction with the accompanying drawings, wherein:

DETAILED DESCRIPTION OF THE PREFERRED EMBODIMENT

Figure 1:
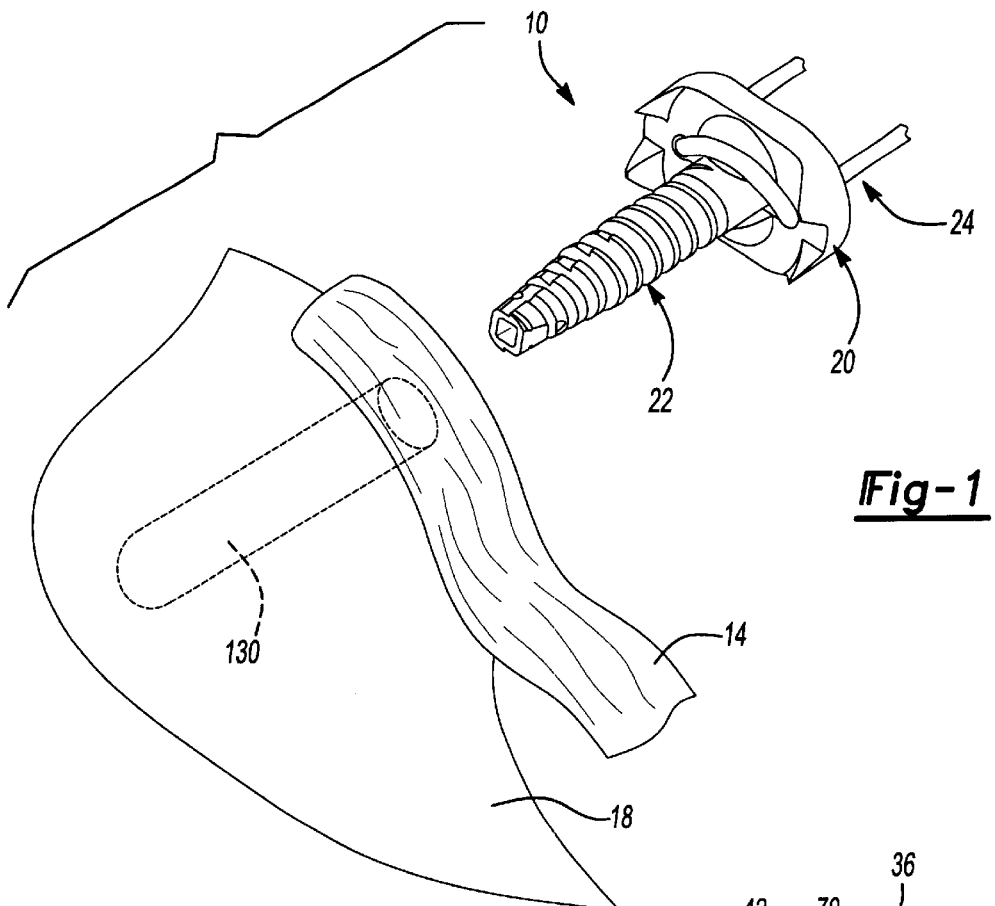
FIG. 1 is a perspective view of a soft tissue securing device constructed in accordance with the teachings of the present invention in association with the bone and soft tissue of a body.

With reference to FIG. 1 of the drawings, a soft tissue securing device constructed in accordance with the teachings of the present invention is generally indicated by reference number 10. Soft tissue securing device 10 is operable for securing a soft tissue 14 to a bone 18. Soft tissue securing device 10 is illustrated to include a fixation device 20 and a screw 22. Those skilled in the art will understand that soft tissue securing device 10 may optionally include a suture 24 as will be discussed in greater detail below. Those skilled in the art will also understand that fixation device 20 and screw 22 may be formed from a resorbable material of the types that are well known in the art so as to permit fixation device 20 and screw 22 to biodegrade generally within the time span of the healing process.

Figure 2:
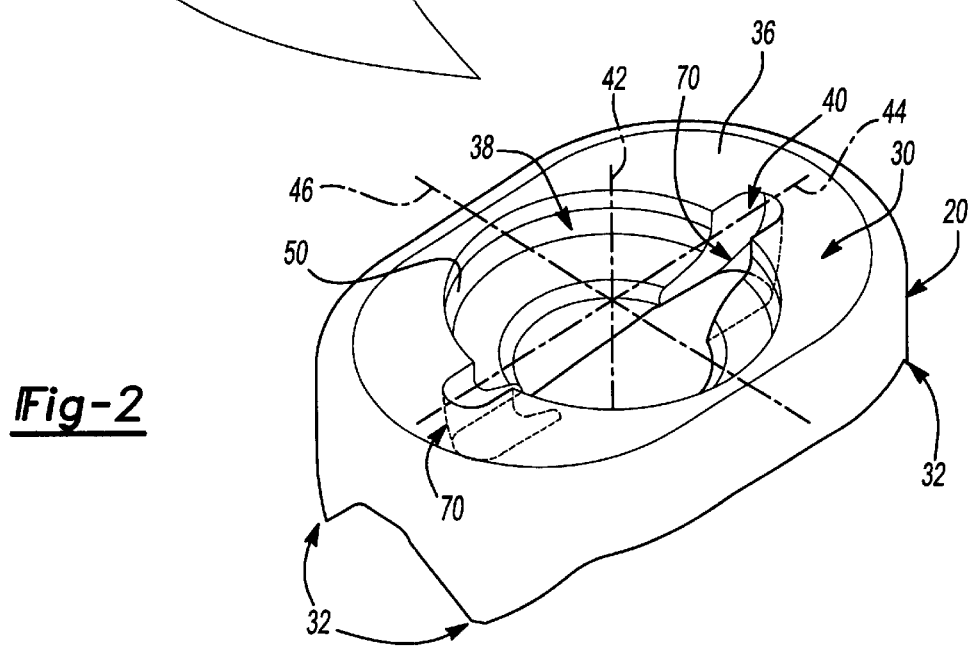
FIG. 2 is a top perspective view of a portion of the soft tissue securing device of FIG. 1 illustrating the fixation device in greater detail.
Figure 3:
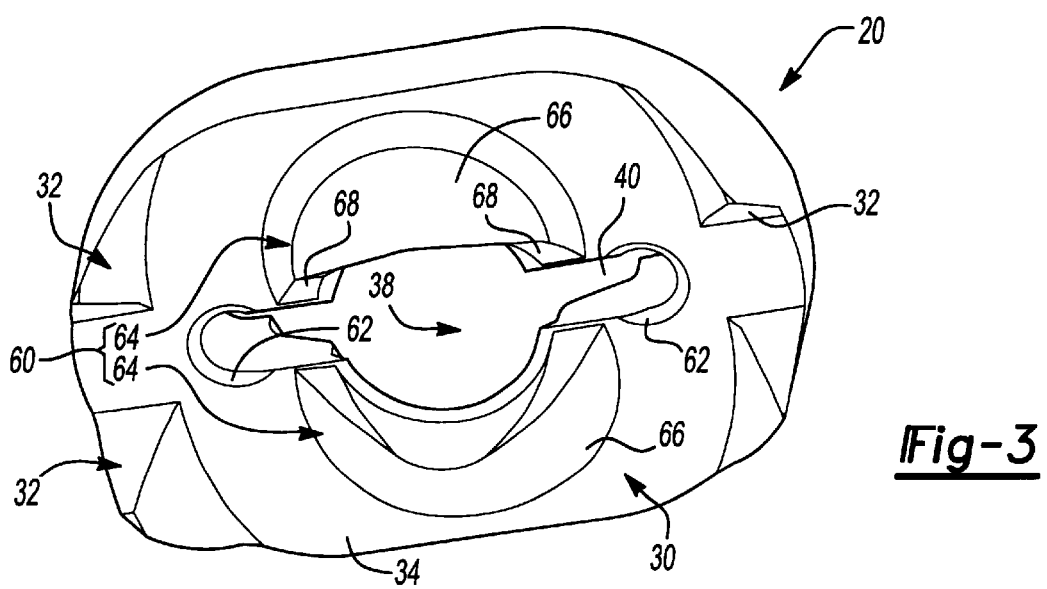
FIG. 3 is a bottom perspective view of the fixation device.

In FIGS. 2 and 3, fixation device 20 is shown to include a body portion 30 and a plurality of teeth 32. Body portion 30 is shown to include a proximal face 34, a distal face 36, a central aperture 38 and a suture slot 40. Body portion 30 has a cross section that is perpendicular to a longitudinal axis 42 of central aperture 38. The cross section is configured to have a first distance along a first axis 44 and a second distance along a second axis 46, with the first distance being greater in magnitude than the second distance. Although the particular cross sectional illustrated has an oval shape, those skilled in the art will understand that body portion 30 may be formed with another cross sectional shape (e.g., rectangular). Construction of body portion 30 in this manner provides a relatively large "foot print" while enabling fixation device 20 to be oriented in a predetermined manner to thereby reduce or eliminate the possibility that fixation device 20 will impinge on a neighboring bone.

Central aperture 38 is formed through body portion 30 and includes a countersunk portion 50 formed into the distal face 36 of body portion 30. Suture slot 40 is also formed through body portion 30, being arranged to intersect central aperture 38 and sized to receive suture 24.

The plurality of teeth 32 are adapted to engage the soft tissue 14 and are coupled to and protrude from the proximal face 34 of body portion 30. The teeth 32 are configured in a manner to space the proximal face 34 of the body portion 30 apart from the bone 18 to thereby ensure that bodily fluids (e.g., blood) will be able to circulate within the soft tissue 14.

With specific reference to FIG. 3, fixation device 20 also preferably includes a suture guide 60 which is coupled to the proximal face 34 of body portion 30 proximate the central aperture 38 and between the ends 62 of the suture slot 40. In the particular embodiment illustrated, the suture guide 60 includes a pair of guide structures 64, each one of which being positioned on an opposite side of the suture slot 40. Each of the guide structures 64 includes a sloped surface 66 that is adapted for directing the suture 24 around the screw 22 as will be discussed in detail below. A pair of fillets 68 are formed into each of the guide structures 64, with each of the fillets 68 extending from the sloped surface 66 to the suture slot 40. Each of the fillets 68 is adapted to guide the suture 24 around the screw 22 and reduce the concentration of stress in the suture 24. A pair of fillets 70 are also formed into the ends 62 of the suture slot 40 and function to guide the suture 24 into the suture slot.

Figure 4:
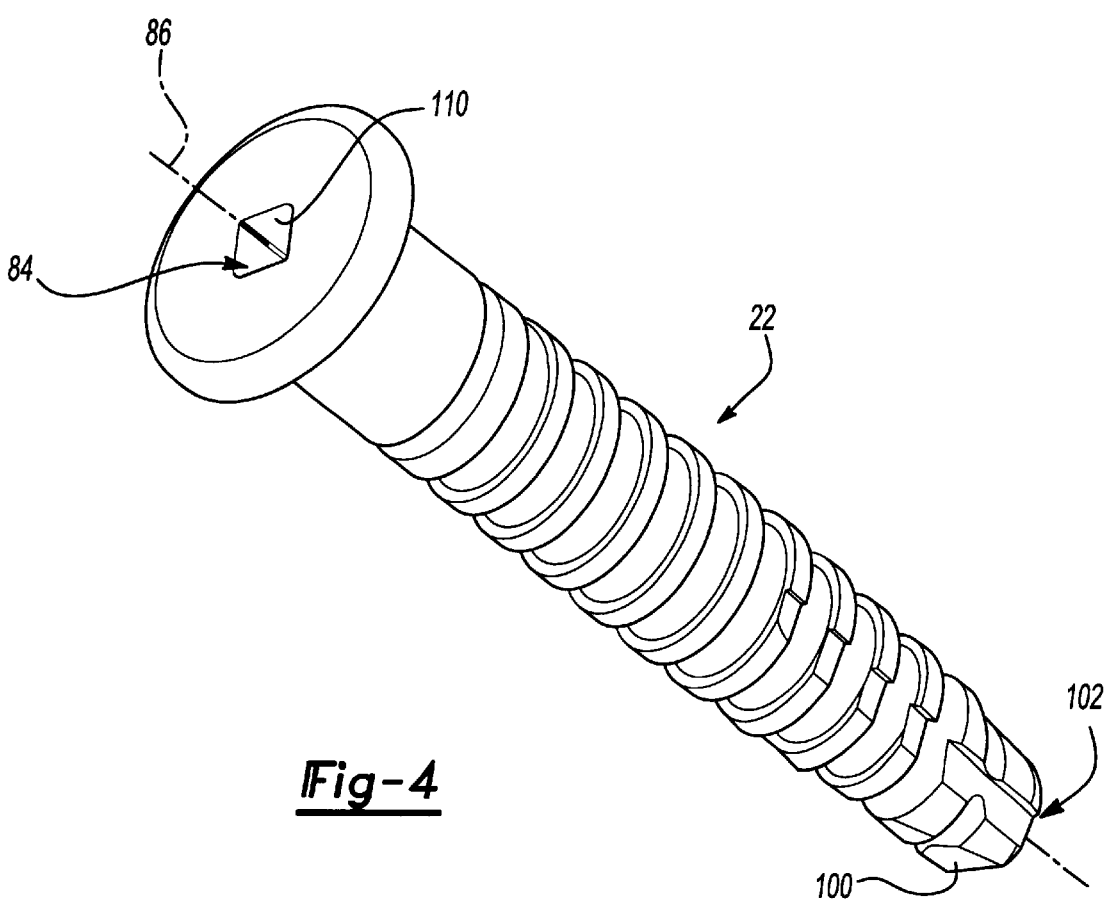
FIG. 4 is a top perspective view of a portion of the soft tissue securing device of FIG. 1 illustrating the screw in greater detail.
Figure 5:
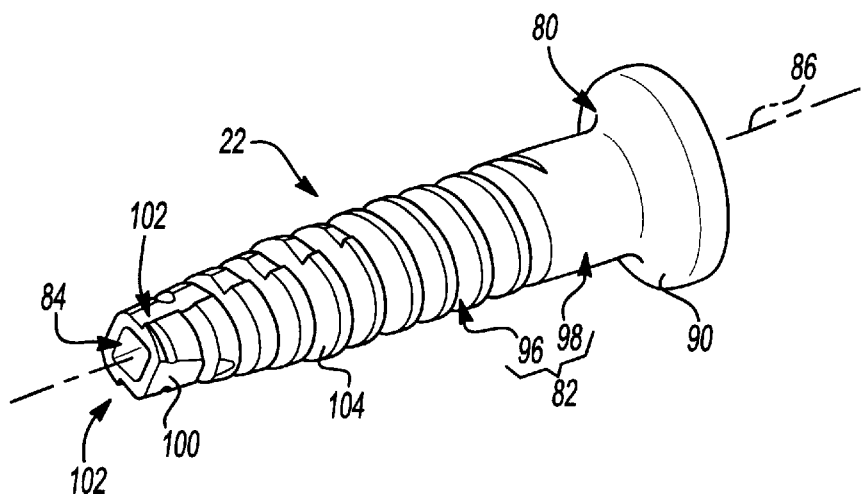
FIG. 5 is a bottom perspective view of the screw.

In FIGS. 4 and 5, the screw 22 is illustrated to include a head portion 80, a body portion 82 and a hollow cavity 84 formed through the screw 22 along its longitudinal axis 86. In the particular embodiment illustrated, the head portion 80 includes a tapered annular flange 90 that is configured to mate with the countersunk portion 50 of the central aperture 38. The tapered annular flange 90 and the countersunk portion 50 are configured to cooperate to provide the fixation device 20 and the screw 22 with a predetermined degree of compliance between the longitudinal axis 42 of the central aperture 38 and the longitudinal axis 86 of the screw 22. As such, the longitudinal axis 86 of the screw 22 may be skewed within a predetermined amount relative to the longitudinal axis 42 of the central aperture 38 without effecting the performance of the soft tissue securing device 10. Preferably, the countersunk portion 50 and head portion 80 are sized such that the head portion 80 of the screw 22 does not extend past the distal face 36 of the body portion 30 so as to minimize the risk that the soft tissue securing device 10 will not impinge upon another area (e.g., bone).

The body portion 82 is illustrated to include a threaded portion 96 and a cylindrically shaped portion 98 that couples threaded portion 96 to head portion 80. The proximal end of threaded portion 96 is tapered and includes a plurality of flat portions 100 which facilitate the insertion of the screw 22 into a hole (not shown) formed into the bone 18. Threaded portion 96 also includes a plurality of longitudinally arranged recesses 102 which permit the male threads 104 of the threaded portion 96 to cut corresponding female threads (not shown) into the bone 18.

Figure 6A:
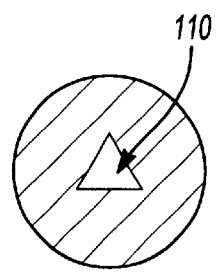
FIGS. 6A, 6B and 6C are cross-sectional view of an alternate embodiment of the screw illustration various non-circular cross sections of the drive portion of the hollow cavity.
Figure 6B:
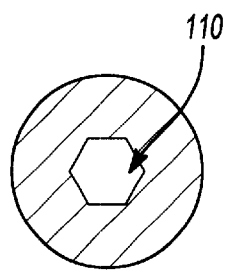
Figure 6C:
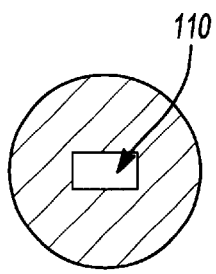

The hollow cavity 84 includes a drive portion 110, which in the particular embodiment illustrated, has a generally square cross section. Those skilled in the art will understand, however, that drive portion 110 may be formed with any non-circular cross-section which facilitates the transmission of torque to the screw 22, such as the configurations illustrated in FIGS. 6A through 6C to permit the screw 22 to be installed to the bone. Preferably, the drive portion 110 extends over substantially the entire length of the hollow cavity 84 to permit the installation torque to be distributed over a relative large portion of the screw 22, thereby minimizing the risk that the drive portion 110 will be stripped (i.e., rounded out) during the installation of the screw 22.

Figure 7:
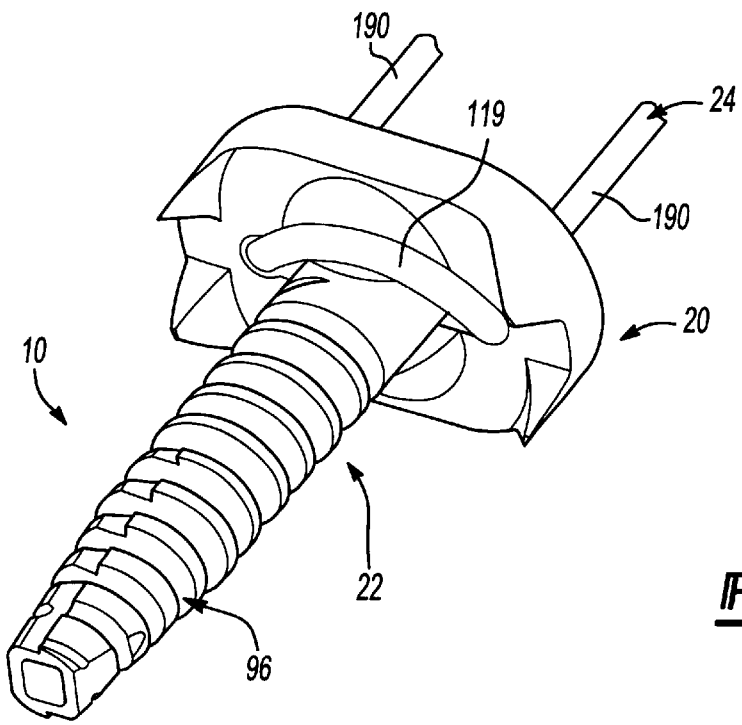
FIG. 7 is a bottom perspective view of the soft tissue securing device of FIG. 1 as subassembled prior to its implant in a body.

In FIG. 7, the preparation of the soft tissue securing device 10 is illustrated. A loop 119 formed in the suture 24 is inserted into the fixation device 20 through the suture slot 40. The threaded portion 96 of the screw 22 is next aligned to the central aperture 38 and the screw 22 is inserted therethrough.

Figure 8:
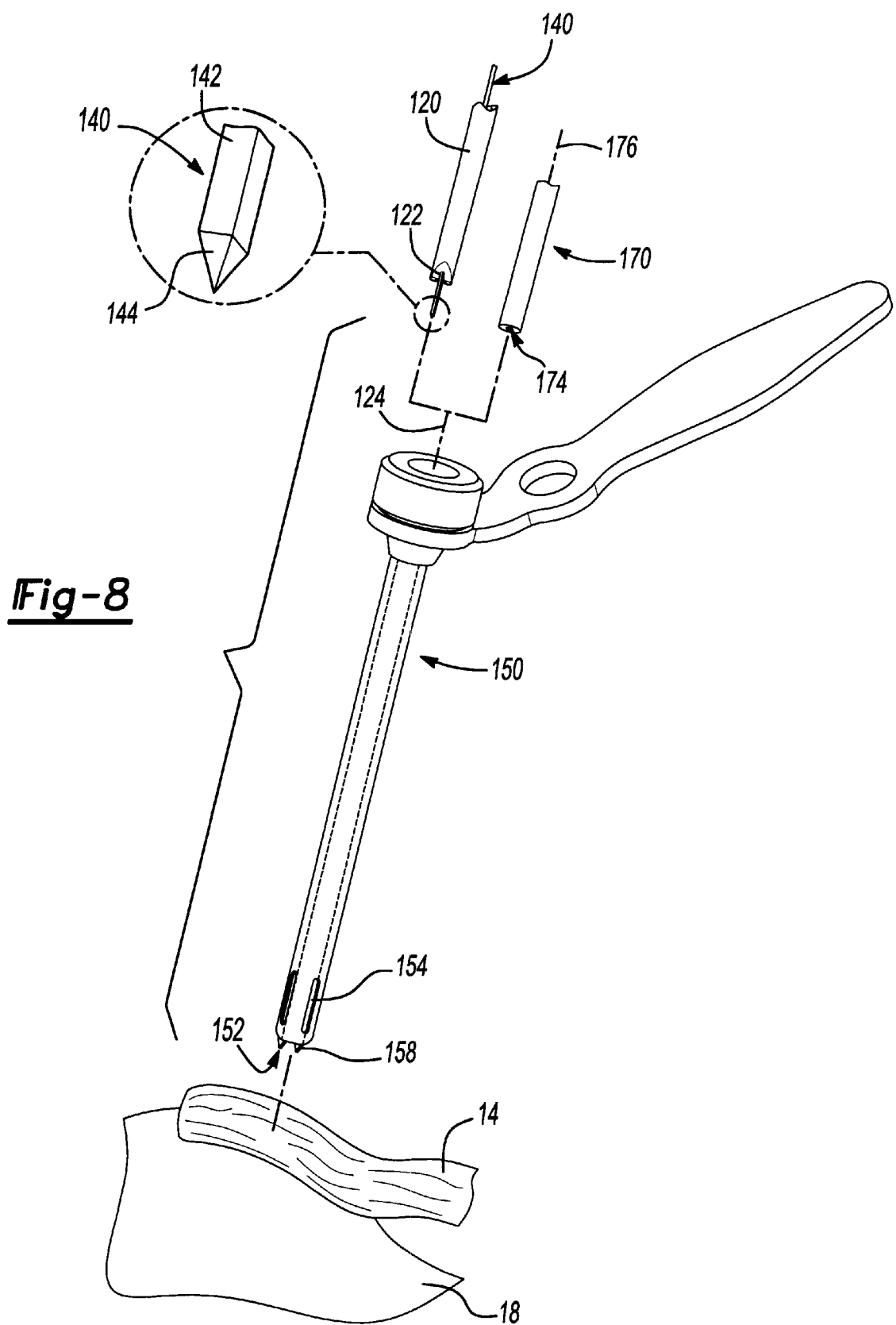
FIG. 8 is an exploded perspective view of the soft tissue securing device of FIG. 1 in operative association with the set of installation tools.

In FIG. 8, a cannulated drill 120 having a guide aperture 122 formed therethrough along the longitudinal axis 124 of the drill 120 is illustrated in association with the bone 18. The drill 120 is employed to form the hole 130 in the bone 18 into which the screw 22 will be inserted. A guide member 140 having a driver portion 142 that is configured to match the drive portion 110 of the hollow cavity 84 is shown to extend through the guide aperture 122. The guide member 140 includes a pointed tip 144 which may be employed to position the drill 120 to a predetermined position prior to and during the formation of the hole 130 (shown in FIG. 1).

Figure 9:
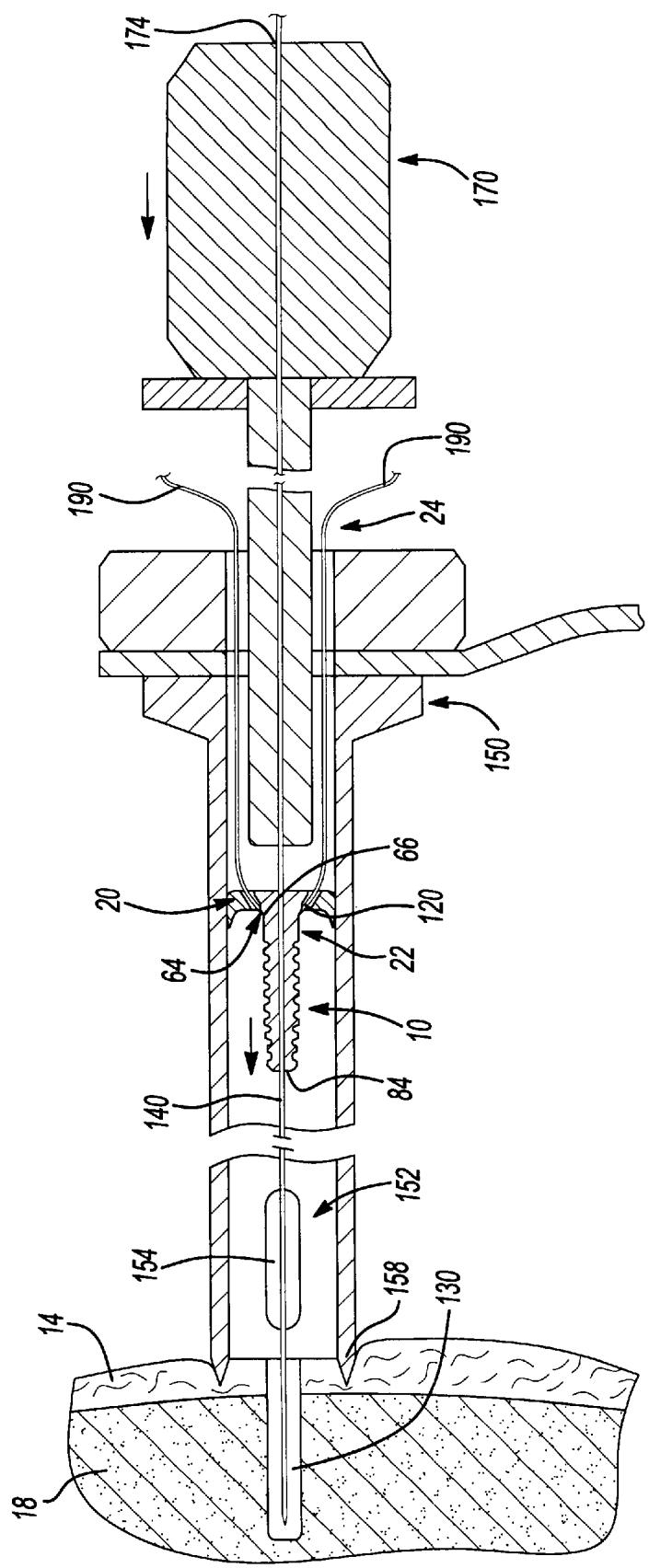
FIG. 9 is a longitudinal cross section of the soft tissue securing device of FIG. 1 in operative association with the set of installation tools illustrating the installation of the soft tissue securing device of FIG. 1.
Figure 10:
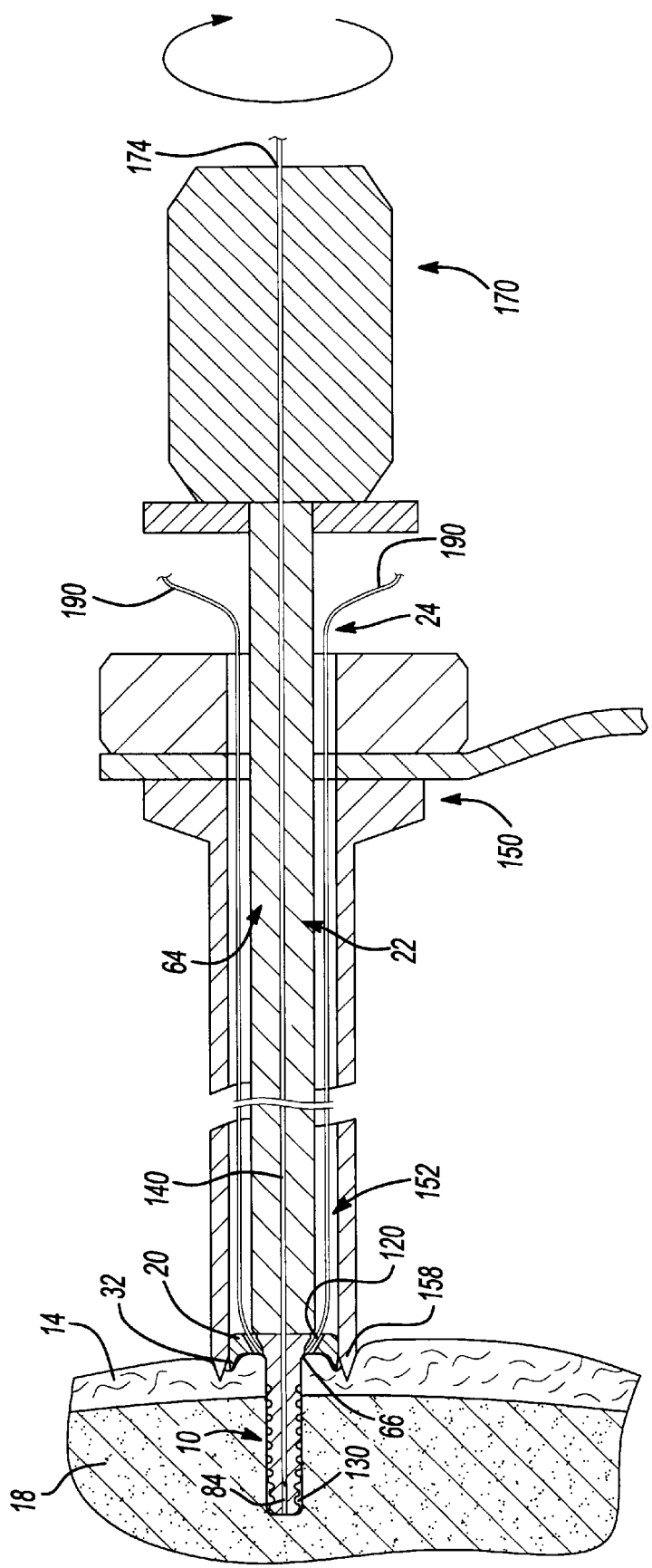
FIG. 10 is a longitudinal cross section of the soft tissue securing device of FIG. 1 as installed to a patient.

As shown in FIGS. 9 and 10, the guide member 140 is pushed into the hole 130 after the hole 130 has been formed in the bone 18. Those skilled in the art will understand that the step of forming the hole 130 and the step of pushing the guide member 140 into the hole 130 may be performed substantially simultaneously. The drill 120 is then removed from the hole 130 while maintaining the guide member 140 in the hole 130.

An optional guide cannula 150 having a non-circular longitudinal bore 152 that is configured to match at least a portion of the perimeter of the fixation device 20 may be employed if the fixation device 20 is to have a predetermined orientation relative to the bone 18. The longitudinal bore 152 is aligned to the guide member 140 and translated thereon until the guide cannula 150 is in contact with the soft tissue 14. Preferably, the guide cannula 150 is rotated to the desired orientation prior to its contact with the soft tissue 14. In the particular embodiment illustrated, guide cannula 150 includes a plurality of viewing windows 154 that are formed through guide cannula 150 and permit the surgeon to view the soft tissue securing device 10 during its attachment to the soft tissue 14 and the bone 18. The guide cannula 150 is also shown to include a plurality of teeth 158 which are configured to engage the soft tissue 14 to prevent its movement relative to the bone 18. Those skilled in the art will understand that the guide cannula 150 may be additionally or alternatively employed to position the drill 120 prior to the formation of the hole 130.

The prepared soft tissue securing device 10 is next positioned such that the hollow cavity 84 of the screw 22 is aligned to the guide member 140 and the fixation device 20 is aligned to the longitudinal bore 152 in the guide cannula 150. With additional reference to FIG. 8, a driver 170 having a bore 174 formed through its longitudinal axis 176 is inserted into the longitudinal bore 152 in the guide cannula 150 such that the guide member 140 is disposed through the bore 174. The driver 170 is then employed to simultaneously push the screw 22 along the guide member 140 and the fixation device 20 through the longitudinal bore 152 until the screw 22 contacts the bone 18. The bore 174 in the driver 170 is preferably configured to mate with the driver portion 142 of guide member 140 so that rotation of the driver 170 rotates the guide member 140, causing the screw 22 to rotate and threadably engage the hole 130 in the bone 18. Engagement of the screw 22 into the hole 130 generates a clamping force which is exerted onto the fixation device 20, thereby causing the teeth 32 to engage the soft tissue 14 and the fixation device 20 to retain the soft tissue 14 in a stationary position relative to the bone 18. The pressure exerted by fixation device 20 onto the soft tissue 14 may be fine-tuned by further tightening or loosening the screw 22.

Once the fixation device 20 is firmly secured to the bone 18, the surgeon is able to apply tension to the ends 190 of the suture 24. The tensioning of the ends 190 of the suture 24 causes the looped portion 119 of the suture 24 to slide on one of the sloped surface 66 of the guide structure 64 toward the screw 22. As the clearance between the screw 22 and the guide structure 64 is sufficiently small, the suture 24 is lodged between the side of the screw 22 and the end of the guide structure 64, thereby eliminating the need to tie the suture 24 directly to the fixation device 20. Thereafter, the suture 24 may be employed in a manner that is well known in the art to further aid in the securing of the soft tissue 14 to the bone 18.

Those skilled in the art will understand that the use of cannulated drill 120 and guide cannula 150 is merely exemplary and not intended to limit the scope of the present invention in any manner. Accordingly, those skilled in the art will understand that the soft tissue securing device 10 of the present invention may also be used in a non-cannulated procedure wherein the hole 130 is formed into the bone 18 with a non-cannulated drill (not shown). In procedures of this type the tip 144 of the guide member 140 is then employed to probe for the hole 130 with or without the aid of the guide cannula 150. Once the tip 144 of the guide member 140 is positioned into the hole 130, the hollow cavity 84 is positioned over the guide member 140, and the driver 170 is employed to position the screw 22 in contact with the bone 18 and to rotate the guide member 140 as discussed above.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A fixation device for engaging soft tissue in a body, the fixation device comprising:
    a body portion having a proximal face and a distal face, the body portion including a central aperture formed through the proximal and distal faces, the central aperture being adapted to receive a screw, the body portion also including a suture slot having a first end and a second end, the suture slot intersecting the central aperture and being adapted to receive a suture;
    a plurality of teeth extending from the proximal face of the body portion and adapted to engage the soft tissue; and
    a suture guide associated with the proximal face of the body portion, the suture guide extending at least partially between the ends of the suture slot.

2. The fixation device of claim 1, wherein the central aperture includes a countersunk portion formed into the distal face of the body portion, the countersunk portion being adapted to receive a mating tapered portion of the screw.

3. The fixation device of claim 1, wherein the suture guide includes at least one guide structure, the guide structure being positioned alongside the suture slot and having a sloped surface that is adapted for directing the suture around the screw and preventing the suture from passing out of the suture slot when the screw extends into the central aperture.

4. The fixation device of claim 3, wherein a pair of fillets are formed into each of the guide structures, each of the fillets extending from the sloped surface to the suture slot, the pair of fillets being adapted to guide the suture around the screw and into the suture slot.

5. The fixation device of claim 3, wherein two of the guide structures cooperate to limit an amount by which the plurality of teeth are permitted to engage the soft tissue.

6. The fixation device of claim 1, wherein the fixation device is formed from a resorbable material.

7. The fixation device of claim 1, wherein a fillet is formed into each end of the suture slot, each of the fillets being adapted to guide the suture around the screw and into the suture slot.

8. The fixation device of claim 1, wherein the fixation device has a cross section that is taken in a direction perpendicular to a longitudinal axis of the central aperture, the cross section being configured to have a first distance along a first axis and a second distance along a second axis and wherein the first distance is greater in magnitude than the second distance.

9. The fixation device of claim 8, wherein the cross section of the body portion is oval in shape.

10. A soft tissue securing device for securing a soft tissue of a body to a bone, the soft tissue securing device comprising:

a suture having a looped section and a pair of ends;

a fixation device having a body portion and a plurality of teeth, the body portion including a proximal face, a distal face, a central aperture and a suture slot having a first end and a second end, the central aperture being formed through the proximal and distal faces, the suture slot intersecting the central aperture and receiving the looped section of the suture, the plurality of teeth coupled to the proximal face of the body portion and adapted to engage the soft tissue; and a screw disposed through the central aperture;

wherein the looped section of the suture is disposed at least partially around the screw and transmits a load thereto in response to the application of tension to the ends of the suture.

11. The soft tissue securing device of claim 10, wherein the fixation device further includes a suture guide, the suture guide coupled to the proximal face of the body portion, the suture guide extending between the ends of the suture slot and abutting the screw and wherein the suture guide guides the suture around a side of the screw in response to the application of tension to the ends of the suture.

12. The soft tissue securing device of claim 10, wherein the screw includes a head portion having a tapered annular flange and the central aperture of the body portion includes a countersunk portion formed into the distal face, the annular flange and the countersunk portion providing a predetermined degree of compliance between a longitudinal axis of the central aperture and a longitudinal axis of the screw.

13. The soft tissue securing device of claim 10, wherein the screw includes a hollow cavity formed therethrough along a longitudinal axis of the screw, at least a portion of the hollow cavity having a non-circular cross section.

14. The soft tissue securing device of claim 13, wherein the non-circular cross section extends substantially the entire length of the hollow cavity.

15. The soft tissue securing device of claim 10, wherein the suture guide includes at least one guide structure that is positioned alongside of the suture slot, the guide structure having a sloped surface that is adapted for directing the suture around the screw and preventing the suture from passing out of the suture slot when the screw extends into the central aperture.

16. The soft tissue securing device of claim 15, wherein a pair of fillets are formed into each of the guide structures, each of the fillets extending from the sloped surface to the suture slot, the pair of fillets being adapted to guide the suture around the screw and into the suture slot.

17. The soft tissue securing device of claim 10, wherein the fixation device and the screw are formed from a resorbable material.

18. The soft tissue securing device of claim 10, wherein the fixation device has a cross section that is taken in a direction perpendicular to a longitudinal axis of the central aperture, the cross section being configured to have a first distance along a first axis and a second distance along a second axis and wherein the first distance is greater in magnitude than the second distance.

19. The soft tissue securing device of claim 18, wherein the cross section of the body portion is oval in shape.

20. The soft tissue securing device of claim 10, wherein a fillet is formed into each end of the suture slot, each of the fillets being adapted to guide the suture around the screw and into the suture slot.

* * * * *